US008584676B2

(12) United States Patent
Gossweiler

(10) Patent No.: US 8,584,676 B2
(45) Date of Patent: Nov. 19, 2013

(54) BREATH RESPONSIVE FILTER BLOWER RESPIRATOR SYSTEM

(75) Inventor: Otto Gossweiler, Effretikon (CH)

(73) Assignee: Immediate Response Technologies, Glenn Dale, MD (US)

( * ) Notice: Subject to any disclaimer, the term of this patent is extended or adjusted under 35 U.S.C. 154(b) by 2840 days.

(21) Appl. No.: 10/715,861

(22) Filed: Nov. 19, 2003

(65) Prior Publication Data

US 2005/0103343 A1    May 19, 2005

(51) Int. Cl.
*A62B 18/08* (2006.01)
*A62B 7/10* (2006.01)
*A62B 18/02* (2006.01)

(52) U.S. Cl.
USPC ............ 128/206.12; 128/206.15; 128/206.16; 128/206.17; 128/206.18; 128/206.21

(58) Field of Classification Search
USPC ............ 128/206.12, 206.15, 206.16, 206.17, 128/206.18, 206.21
See application file for complete search history.

(56) References Cited

U.S. PATENT DOCUMENTS

| 865,996 A | 9/1907 | Catt |
|---|---|---|
| 1,105,127 A | 7/1914 | Drager |
| 1,169,996 A | 2/1916 | Prindle |
| 3,018,776 A | 1/1962 | Saitta |
| 3,044,464 A | 7/1962 | Gray |
| 3,715,032 A | 2/1973 | Nicko |
| 3,731,717 A | 5/1973 | Potash |
| 3,852,196 A | 12/1974 | Szpur |
| 3,990,439 A | 11/1976 | Klinger |
| 4,243,029 A | 1/1981 | Apple |
| 4,257,415 A | 3/1981 | Rubin |
| 4,384,576 A | 5/1983 | Farmer |
| 4,402,316 A | 9/1983 | Gadberry |
| 4,433,684 A | 2/1984 | Sarnoff |
| 4,493,614 A | 1/1985 | Chu |
| 4,513,741 A | 4/1985 | Demi |
| 4,529,514 A | 7/1985 | Gruett |
| 4,574,799 A | 3/1986 | Warnke |
| 4,676,236 A * | 6/1987 | Piorkowski et al. ..... 128/201.23 |
| 4,682,993 A | 7/1987 | Todd |
| 4,823,785 A | 4/1989 | Mancosu |
| 4,827,964 A * | 5/1989 | Guido et al. ................. 137/81.1 |
| 4,841,963 A | 6/1989 | Vandeputte |
| 4,915,106 A | 4/1990 | Aulgur |

(Continued)

FOREIGN PATENT DOCUMENTS

DE    4241033 A1    6/1994
WO    2005035365 A2    4/2005

(Continued)

*Primary Examiner* — Patricia Bianco
*Assistant Examiner* — Nihir Patel
(74) *Attorney, Agent, or Firm* — Duane Morris LLP

(57) ABSTRACT

A breath responsive filter blower respirator system for a gas mask including a pressure and control device, such as an optoelectric device and/or a pressure sensor, to control the air flow produced by an air blower. The optoelectric device detects the position of the mask's outflow valve. The pressure sensor measures air pressure in the mask relative to ambient air or the absolute air pressure in the mask. During exhalation, the pressure detector detects an increase in air pressure in the mask and/or the optoelectric device detects the outflow valve in an open position, and then signals the central processing unit to signal the air blower to reduce speed. The reduction in speed reduces air flow in the mask and lowers air pressure in the mask.

15 Claims, 2 Drawing Sheets

(56) References Cited

U.S. PATENT DOCUMENTS

| | | |
|---|---|---|
| 4,924,861 A | 5/1990 | Kiske |
| 4,936,298 A | 6/1990 | Nishina |
| 4,961,420 A | 10/1990 | Cappa |
| 4,971,051 A | 11/1990 | Toffolon |
| 5,036,846 A | 8/1991 | Aulgur |
| 5,065,745 A | 11/1991 | Meier |
| 5,209,226 A | 5/1993 | Goodley |
| 5,235,972 A | 8/1993 | Strong |
| 5,427,091 A | 6/1995 | Phillips |
| 5,503,147 A | 4/1996 | Bertheau |
| 5,509,406 A * | 4/1996 | Kock et al. ............... 128/203.14 |
| 5,690,102 A | 11/1997 | Bertheau |
| 5,914,037 A | 6/1999 | Yen |
| 5,950,621 A * | 9/1999 | Klockseth et al. ....... 128/204.26 |
| 6,039,045 A | 3/2000 | Bertheau |
| 6,155,258 A | 12/2000 | Voege |
| 6,214,074 B1 | 4/2001 | Silviera |
| 6,269,811 B1 | 8/2001 | Duff et al. |
| 6,325,116 B1 | 12/2001 | Savage |
| 6,615,828 B1 | 9/2003 | Petherbridge |
| 6,622,724 B1 * | 9/2003 | Truitt et al. ............... 128/204.18 |
| 6,659,101 B2 * | 12/2003 | Berthon-Jones ......... 128/204.21 |
| 6,796,304 B2 | 9/2004 | Odell et al. |
| 6,823,867 B2 | 11/2004 | Avery et al. |
| 6,834,650 B1 | 12/2004 | Fini et al. |
| 6,837,239 B2 | 1/2005 | Beizndtsson et al. |
| 7,101,412 B2 | 9/2006 | Gossweiler |
| 7,195,015 B2 * | 3/2007 | Kuriyama ................ 128/205.12 |
| 2002/0014236 A1 * | 2/2002 | Dittmann et al. ......... 128/203.25 |
| 2003/0005932 A1 | 1/2003 | Rydgren |
| 2005/0051235 A1 | 3/2005 | Kline |
| 2005/0126572 A1 | 6/2005 | Gossweiler |
| 2005/0263155 A1 | 12/2005 | Gossweiler |
| 2006/0048782 A1 | 3/2006 | Gossweiler |

FOREIGN PATENT DOCUMENTS

| | | |
|---|---|---|
| WO | 2005055912 A2 | 6/2005 |
| WO | 2005060374 A2 | 7/2005 |
| WO | 2005061076 A2 | 7/2005 |
| WO | 2005118072 A1 | 12/2005 |
| WO | 2006028467 A2 | 3/2006 |

* cited by examiner

BREATH RESPONSIVE FILTER BLOWER RESPIRATOR SYSTEM

BACKGROUND OF THE INVENTION

1. Field of the Invention

The present invention relates to a pneumatic and electronic control system for an electronically powered air purifying respirator system.

2. Description of Related Art

Respiratory devices, such as protection masks, also interchangeably referred to herein as gas masks or masks, are well known. Civilians, law enforcement, military personnel, fire fighters and other groups of individuals commonly referred to as first responders, hereinafter referred to as users, wear masks for protection from an environment containing harmful and possibly fatal air-born toxins or any other such hazardous material. Such toxins and materials are hazardous to respiratory systems and generally take the form of harmful gases, vapors, and particulate matter. The respiratory hazards may also include various agents, such as nuclear, biological and chemical (NBC) agents, which may be in the form of particulates, vapors or aerosols.

One type of breathing apparatus, known as a Powered Air Purifying Respirator (PAPR), is a fan-forced positive pressure breathing apparatus. PAPRs are used in environments where the ambient air is relatively oxygen-rich and where filtering elements are effective in removing all contaminants from the ambient air before the ambient air enters the gas mask. PAPRs typically include a gas mask, a filtering element to remove contaminants from ambient air, a blowing element, such as a fan and a power source to provide operational power to the blowing element. The fan or blowing element continuously supplies filtered air to the gas mask. The filtered air replenishes the internal space of the mask, and exhaled air, also known as spent air, is continually ejected.

Conventional PAPRs have numerous drawbacks that limit their applicability. For example, the continuous supply of filtered air to the user is highly inefficient and wasteful because the user is unable to ingest and/or inhale all of the continuously filtered air, which is fed into the internal space of the gas mask. It is well understood to those skilled in the art that during exhalation, the user cannot ingest or inhale the filtered air. However, even during exhalation, filtered air continually enters the internal space of the mask in typical PAPRs. As a result, air exhaled by the user and some amount of unused, filtered air driven into the internal space of the mask by the blowing element are expelled from the mask during the exhalation phase of the user's breathing cycle. Thus, the PAPR exerts resources, specifically energy from the power source, to supply filtered air into the internal space of the mask without a productive or otherwise efficient use of that air, such as ingestion or inhalation by the user.

Another limitation of conventional PAPR's is that the air exhaled by the user and the filtered air driven into the internal space of the mask by the blowing element, respectively, flow in opposite or at least countervailing directions relative to each other within the internal space of the mask. The opposite air flow creates counteracting forces in the internal space of the mask. As a result, the user's workload to draw, inhale, or ingest filtered air during breathing increases. The increased breathing workload means that the user endures difficulty while breathing and is otherwise uncomfortable while using such conventional PAPRs.

Another drawback of conventional PAPRs include the continuous supply of filtered air creating undue wear and tear on the working components of the PAPR. Moreover, the continuous operation of the components that filter the air supplied to the internal space of the mask typically results in mechanical breakdown of the components of the PAPR. The more the components of the PAPR are used, the more frequent such breakdowns are likely to occur. For example, the filtering element becomes full of contaminants over time and must be replaced. Replacement of the filter directly correlates to the amount of air to be filtered. Typically, in conventional PAPRs, air is continually pumped to the internal space of the mask. The filter required to remove contaminants from the ambient air works continually as well. Accordingly, the filter requires frequent and regular replacement. If the air requiring filtering were to be intermittently supplied when needed by the user, the filter would have to be replaced less frequently.

A similar situation exists with respect to the power supply of conventional PAPRs. An energy source with limited capacity to generate power is typically used to drive the filtering components. In general, the amount of reserve power available in an energy source of the conventional PAPR is inversely proportional to the amount of air being filtered and driven by the blowing element. Typically, in conventional PAPRs, the energy source for the PAPR is constantly used, and reserves are exhausted, as the continual filtering of the supply of air to the mask occurs. Less power from the energy source is used if the air is intermittently filtered. The less power used, the more battery power that is conserved. As a result, the battery has longer life and is ultimately replaced less often with intermittent filtering.

There is a need for a PAPR mask that improves the air flow within the mask and facilitates breathing for the user. There is a further need for a PAPR mask that conserves power and extends the life of the energy source powering the mask.

SUMMARY OF THE INVENTION

Aspects of the present invention provide a pneumatic and electronic performance control, to be used in conjunction with a PAPR, that reduces the air pressure in a respirator mask and helps the user to exhale in the mask. Furthermore, aspects of the present invention increase the operational life of the power source used with the present invention.

One aspect of the present invention relates to a breath responsive filter blower PAPR having an electronic performance control system, e.g., logic on a printed circuit board (also interchangeably referred to herein as a PC Board or PCB), as is known in the art, to produce the functions indicated having such logic may also be performed using other electrical or electronic devices known in the art. The electronic performance control system has an optoelectric device, which detects the position of the mask outflow valve to determine whether to adjust, i.e., increase or decrease, airflow from the blower to the respiratory mask. Additionally, the optoelectric device transmits electrical signals through electrical lines to a processor or a PCB, which, in turn, processes the signal. The blower is either activated or deactivated depending on the signal processed by the PCB.

Another aspect of the present invention relates to a breath responsive filter blowing PAPR having a pneumatic performance control system. The pneumatic performance control system has a pressure sensor that measures the pressure inside the respirator mask. In one variation, the pressure sensor measures the absolute air pressure in the mask. In another variation, the pressure sensor measures the relative pressure of air pressure in the mask compared to ambient air pressure.

In still an additional aspect of the invention, a respiratory protective system includes a filter, a facepiece, a breathing hose, and a breath-responsive air-filtering respiratory protective blower having an optoelectric device that detects the position of the mask outflow valve. The optoelectric device modulates the air flow inside the mask by causing operation of the filter when the outflow valve is in an open position.

Additional advantages and novel features of the present invention will become more apparent from the following description.

DETAILED DESCRIPTION OF THE PRESENT INVENTION

The invention disclosed herein improves the state of PAPR technology. In operation a pressure sensor and optoelectronic device of the present invention work individually or cooperatively to detect air pressure in a gas mask and to send informational signals to a processor. The processor receives the informational signals, interprets the signals, and transmits subsequent signals to turn-on/turn-off or increase/decrease air flow from an air blower. When the pressure of filtered air in the gas mask is at a relatively high level, which makes it difficult for the user to breathe, the transmitted signals are used to instruct the air blower to cease or reduce air flow to the mask. Conversely, when the pressure in the mask reaches a predetermined and relatively low level, the transmitted signals are used to instruct the air blower to increase air flow to the mask. In addition, to enhance the ability of the user to breathe, the present invention facilitates an increased operational time for the PAPR. Unlike conventional PAPRs, which typically operate an air blower continuously, the present invention allows for controlled and intermittent use of the air blower. As a result, less power is required to operate the air blower, and the energy of the power source is prolonged for a greater length of time.

Figure 1:
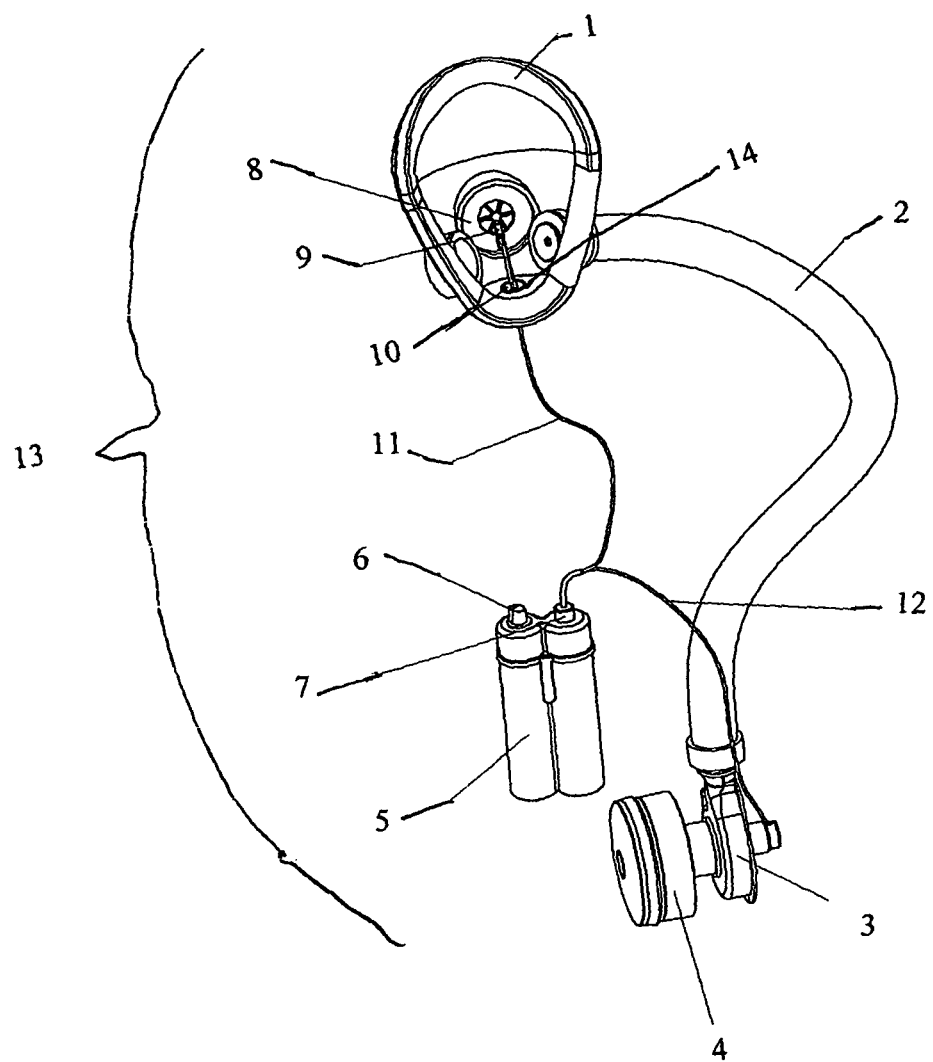
FIG. 1 is a perspective view of a breath responsive filter blower respirator system for an electrically powered PAPR having an optoelectric device and air pressure sensor, in accordance with one embodiment of the present invention.
Figure 2:
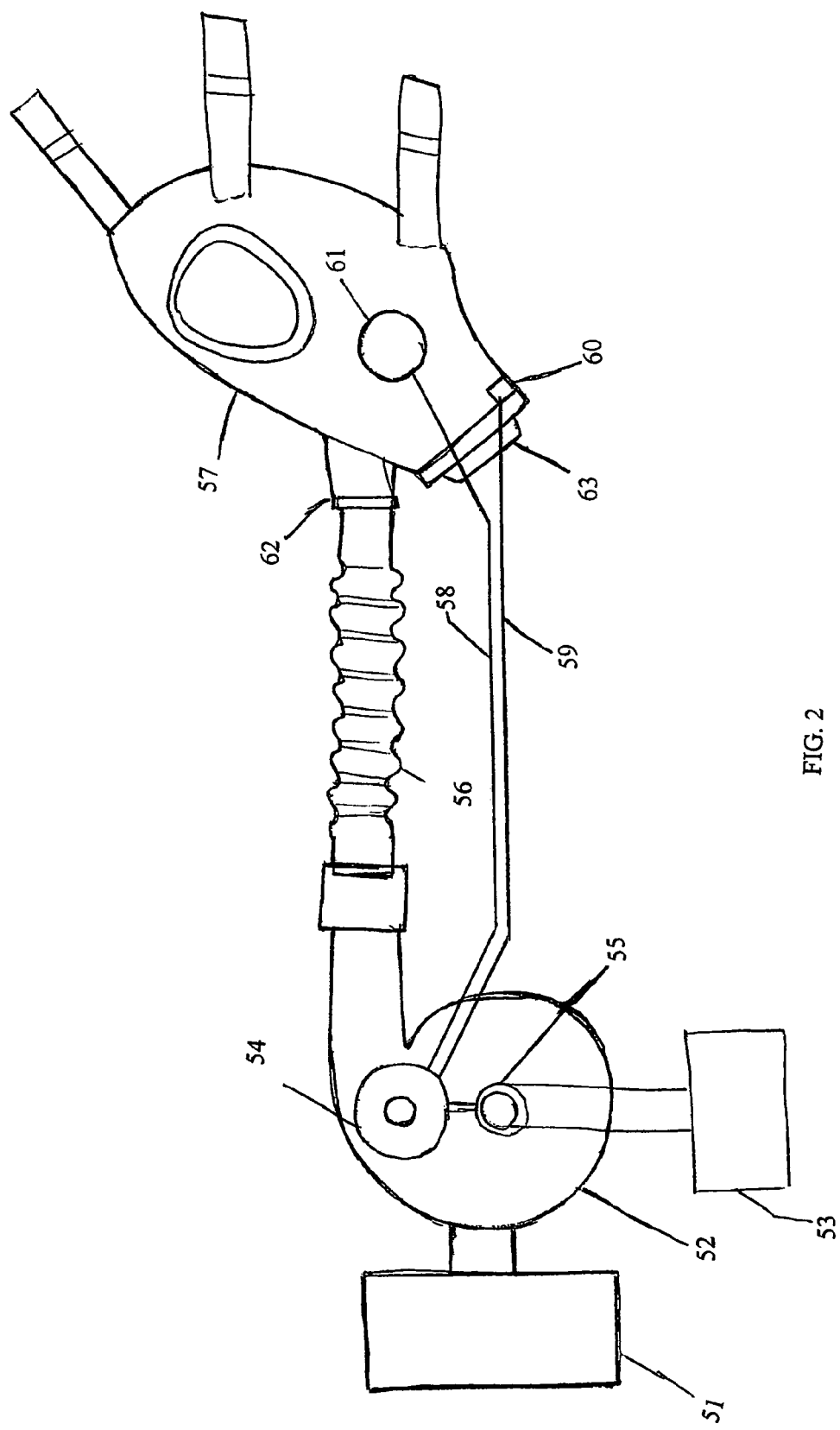
FIG. 2 is a schematic diagram of a breath responsive filter blower respirator, including the filter, battery powered blower, mask, position detector and pressure sensor, in accordance with one embodiment of the present invention.

The present invention provides a breath responsive filter blower respirator system, which is illustrated in FIGS. 1 and 2. The present invention includes a blower powered by an energy source controlled by a pneumatic and/or electronic control system, which modulates the speed and volume of the filtered air delivery in the gas mask based on the respiration of the user. The present invention helps the user exhale through the PAPR mask by modulating the air flow inside the mask while maintaining a positive pressure in the mask, and decreasing air pressure in the internal space of the mask. The present invention conserves the life of the power source used by activating and deactivating the air blower based on measurements taken by either an optoelectric device or a pneumatic pressure sensor operating individually, or by both devices operating together.

In particular, FIG. 1 illustrates a breath responsive filter blower respirator system 13 according to an embodiment of the present invention. The breath responsive filter blower respirator system 13 includes a gas mask 1, which, for example, covers the face of the user. The shape and structure of the gas mask 1 may be selected from any one of a variety of well known variations in the art. The gas mask 1 covers the entire face of the user. The gas mask 1 of this embodiment may be, for example, rectangular, oblong, or otherwise shaped, so long as the gas mask covers the face, particularly the orifices about the face, (i.e., nasal passages, mouth, etc.) and any exposed facial skin of the user.

In one variation, the mask 1 is connected to an air blower 3 via a breathing air hose 2 to prevent contaminants in the atmosphere or ambient air from entering the breathing zone of a user and to provide a direct, uncontaminable passage between the mask 1 and the blower 3. The breathing air hose 2 is selected from any of a number of such devices that are well known in the art. Although it is within the scope of the present invention to provide a rigid breathing air hose 2, it is preferable in one embodiment that the breathing air hose 2 be flexible. Moreover, it is within the scope of the present invention to form the breathing air hose 2 to be any one of several suitable geometric shapes in cross-section, such as, for example, cylindrical, oval, circular, square, trapezoidal, rectangular, and the like, so long as air is capable of flowing from one fixed point, such as the blower 3, to the another fixed point, such as, the gas mask 1.

A protection filter 4, which is functionally connected to the air blower 3, is exposed to ambient air and allows ambient air to enter the internal portion of the protection filter 4. Presuming the ambient air contains contaminants, the protection filter 4 filters the contaminated ambient air, so as to provide filtered air, which is safe to be consumed by the user. The filtered air exits the protection filter 4 through an opening separate and distinct from the entrance for ambient air to the filter 4. The filtered air from the protection filter 4 thus flows to the air blower 3. The air blower 3 forces the filtered air to the user via the breathing air hose 2 and the gas mask 1.

The power used to move the filtered air in the air blower 3 is generated by a power source 5. The power source 5 includes, for example, solar energy cells, batteries, chemical energy devices or any other energy-producing source. The power source 5 is preferably removable and replaceable. In some embodiments, the power source 5 is connected to the air blower 3 via a coupling 12 capable of conducting electricity.

In some embodiments, the electrical line 12 connects the air blower 3 to the power source 5 via a processing unit 7, interchangeably referred to herein as a processor, PC board or PCB. The processing unit 7 controls operations of the blower 3 by, for example, controlling the transmission of power from the power source 5 to the air blower 3. In one variation, the PCB 7 may be integrated with the power source 5. In another variation, the PCB 7 may be equipped with a manually adjustable blower control knob 6, manipulatable by the user to control the transmission of power from the PCB 7 to the air blower 3. In one variation, the manually adjustable blower control knob 6 is capable of overriding the commands sent by the PCB 7.

In one variation of the invention, the gas mask 1 is equipped with an air pressure sensor 10, preferably positioned in the internal space of the gas mask 1 between the gas mask 1 and the face of the user. The pressure sensor 10 detects and measures the breathing air pressure in the internal space of the gas mask 1. In one variation, the pressure sensor 10 measures the absolute breathing air pressure inside the gas mask 1. In yet another variation, the pressure sensor 10 measures the breathing air pressure inside the gas mask 1 relative to the pressure of ambient air. In this variation, a vent 14 to ambient air is integrally provided with the pressure sensor 10 to allow sensing of the pressure of the ambient air. In one variation, during exhalation, when the pressure inside the mask 1 increases, the pressure sensor 10 transmits a signal to the air blower 3, and the PCB 7, upon receipt of this signal, causes the amount of air flow to the internal space of the gas mask 1 to be reduced by lowering the speed of the blower 3. As a result, the air pressure in the mask 1 is reduced to make exhalation easier for the user. It should be understood that the blower 3 does not have to be turned off completely but may be reduced to a lower air flow so long as positive pressure is being maintained at all times within the mask 1 while being used. At the same time, lowering the speed of the blower 3 results in the power source 5 outputting less energy, thereby resulting in the power source 5 conserving energy and extending the operational life of the system 13.

In one variation, the pressure sensor 10 signal transmitted to the PCB 7 results in the air blower 3 being turned off for a predetermined period of time or until a subsequent signal to turn-on is transmitted by the pressure sensor 10 to the air blower 3. Turn-on may occur during inhalation, for example, as the pressure inside the mask 1 decreases, whereupon the pressure sensor 10 will transmit a turn-on signal to the air blower 3.

The pressure sensor 10 detects and measures the air pressure in the internal space of the gas mask 1. The pressure sensor 10 transmits a pressure measurement signal to the PCB 7 via a coupling 11, which is an element generally known in the art that is capable of conducting signals from the pressure sensor 10 to the PCB 7. The PCB 7 processes the pressure measurement signal and transmits the pressure measurement signal to the air blower 3 or an electrical current, instructing the blower to modulate or otherwise adjust the activity of the blower 3.

In one embodiment of the invention, the gas mask 1 is equipped with an optoelectric device 9 positioned inside of the gas mask 1. In one variation of the present invention, the optoelectric device 9 is positioned on the outside of the gas mask 1. In another variation, the optoelectric device 9 is integrated into the body of the gas mask 1.

The optoelectric device 9 of this embodiment is positioned such that it detects whether the outflow valve 8, which is connected to the gas mask 1, is open or closed. By determining whether the outflow valve 8 is opened or closed, the optoelectric device determines whether to increase or decrease air flow to the gas mask 1 from the air blower 3. For example, during exhalation, when the outflow valve 8 is in the open position, the optoelectric device signals the PCB 7, which in turn causes the air blower 3 to reduce or terminate air flow to the mask 1. It should be understood that the blower 3 does not have to be turned off completely but may be reduced to a lower air flow so long as positive pressure is being maintained at all times within the mask 1 while being used. Conversely, during inhalation, when the outflow valve 8 is in the closed position, the optoelectric device 9 signals (or the lack of signal causes) the PCB 7 to cause the air blower 3 to turn-on or increase air flow to the mask 1. In another variation, the air blower 3 automatically turns on from an initial signal and sends filtered air to the gas mask 1 for only a predetermined amount of time, which, for example, is cyclically repeated corresponding to the breathing cycle of the user.

In one embodiment of the present invention, as illustrated in FIG. 1, the gas mask 1 is equipped with both an optoelectric device 9 and an air pressure sensor 10, which work cooperatively (i.e., in unison or in conjunction with one another) to supply the PCB 7 with information regarding airflow in the mask 1. In one variation, the PCB 7 processes the signal received from the optoelectric device 9 and/or the pressure sensor 10 and transmits a signal to the air blower 3 to cause the blower to turn on or off, or to change speed. In one variation, the user can manually override the signals transmitted by the optoelectric device 9 and the pressure sensor 10 by adjusting the manually adjustable blower control knob 6 or a similar manual adjustment control.

FIG. 2 contains a schematic representation of the breath responsive filter blower respirator of the present invention. A filter 51 is connected to a blower 52, wherein filtered air passes through the filter 51 and flows to the blower 52. The blower 52 operates using energy supplied by an energy source 53, also referred to herein as the power source. The energy source 53 may be, for example, a battery or other portable energy source. In one embodiment, the energy source 53 provides power to a motor 55, which is integral to the blower 52. The motor causes the blower 52 to drive air into a mask 57. The air from the blower 52 is conveyed, via a hose 56, to an inflow member 62 of the gas mask 57.

During exhalation, the pressure in the mask 57 increases and an outflow valve 63 opens to release exhaled air. The pressure sensor 60, also referred to herein as the pressure detector, measures the air pressure of the internal space of the mask 1. When the air pressure inside the mask falls to a predetermined level, the pressure sensor 60 transmits a signal that causes turn-on of the air blower 52. The air blower 52 in turn then drives air to the internal space of the gas mask 1. When the air pressure inside the mask reaches a maximum air pressure, which may, for example, be a predetermined pressure, the pressure sensor 60 transmits a signal to turn-off the air blower 52. During exhalation, for example, when pressure typically rises inside the mask, a signal from the pressure detector 61 results in the blower 52 reducing air flow to the gas mask 1. The signal sent by the pressure sensor 60 may be altered or adjusted using a mode selector 54, via a conductive transfer member, such as a signal wire 58. The mode selector 54 may include a PCB to control operation of the blower 52.

In addition, in some variations, the mask 57 includes an optoelectric device 61, also referred to interchangeably herein as a position detector, which measures the position, i.e., open or closed, of the outflow valve 63. The valve 63 typically moves to an open position during exhalation. The position detector 61 transmits a signal to the mode selector 54 that indicates the position of the valve, which in turn signals the blower 52 to reduce or increase air flow to the mask 1. In one variation of the present invention, the breath responsive filter blower respirator has either the position detector 61 or the pressure sensor 60, or both.

While there has been described what are at present considered to be preferred embodiments of the present invention, it will be understood that various modifications may be made thereto, and it is intended that the appended claims cover all such modifications as fall within the true spirit and scope of the invention. Other modifications will be apparent to those skilled in the art.

What is claimed is:

1. A breath responsive filter blower for a gas mask, comprising:
   a gas mask having a filter port used to provide filtered air;
   a blower operatively connected to the filter port of the gas mask, the blower being capable of forcing air to the gas mask; and,
   a detection and control device operatively connected to the blower which detects a pressure condition within the gas mask and controls operation of the blower wherein the detection and control device comprises:
      a pressure sensor positioned inside the gas mask that detects air pressure in the gas mask; and
      an optoelectric device is positioned in the mask at a location suitable for detecting the open or closed position of an outflow valve linked to the gas mask, wherein the optoelectric device and the pressure sensor work cooperatively, wherein the pressure sensor controls operation of the blower upon exhalation or inhalation of a user of said mask and the optoelectric device controls operation of the blower upon inhalation or exhalation of the user of said mask.

2. The breath responsive filter blower according to claim 1, wherein the optoelectric device and the power source are connected by a coupling.

3. The breath responsive filter blower for a gas mask of claim 1, wherein the optoelectric device detects the outflow valve in the open position, and wherein the optoelectric device transmits a signal to a processor to reduce air flow from the blower upon detecting the open position.

4. The breath responsive filter blower according to claim 3, wherein the processor processes the signal transmitted by the optoelectric device and transmits a signal to the blower.

5. The breath responsive filter blower for a gas mask of claim 4, wherein the signal transmitted by the processor causes the blower to reduce air flow upon detecting the open position.

6. The breath responsive filter blower for a gas mask of claim 1, wherein the optoelectric device detects the outflow valve in the open position, and wherein the optoelectric device transmits a signal to a processor to terminate air flow from the blower upon detecting the open position.

7. The breath responsive filter blower according to claim 6, wherein the processor processes the signal transmitted by the optoelectric device and transmits a signal to the blower.

8. The breath responsive filter blower for a gas mask of claim 7, wherein the processor transmits a signal to the blower to ceases air flow and to terminate the output of power by the power source upon the optoelectric device detecting the open position of the outflow valve.

9. The breath responsive filter blower for a gas mask of claim 1, wherein the optoelectric device detects the outflow valve in the closed position, and wherein the optoelectric device transmits a signal to a processor to increase air flow upon detecting the closed position.

10. The breath responsive filter blower according to claim 9, wherein the processor processes the signal transmitted by the optoelectric device and transmits a signal to the blower upon detecting the closed position.

11. The breath responsive filter blower for a gas mask of claim 10, wherein the optoelectric device detects the outflow valve in the closed position, and wherein the optoelectric device transmits a signal to the processor to activate the blower upon detecting the closed position.

12. The breath responsive filter of claim 1 wherein said pressure sensor detects a predetermined pressure during exhalation of the user and lowers or stops the speed of the blower and said optoelectric device detects a closed position of the outflow valve during inhalation of the user and increases the speed of the blower.

13. The breath responsive filter of claim 1 wherein said pressure sensor detects a predetermined pressure during inhalation of the user and increases the speed of the blower and said optoelectric device detects an open position of the outflow valve during exhalation of the user and lowers or stops the speed of the blower.

14. The breath responsive filter of claim 1 wherein said pressure sensor detects a predetermined pressure during exhalation of the user and lowers or stops the speed of the blower and said optoelectric device detects an open position of the outflow valve during exhalation of the user and lowers or stops the speed of the blower.

15. The breath responsive filter of claim 1 wherein said pressure sensor detects a predetermined pressure during inhalation of the user and increases the speed of the blower and said optoelectric device detects a closed position of the outflow valve during inhalation of the user and increases the speed of the blower.

* * * * *